(12) United States Patent
Lifshitz-Liron

(10) Patent No.: US 7,449,603 B2
(45) Date of Patent: Nov. 11, 2008

(54) PROCESS FOR THE PREPARATION OF CINACALCET BASE

(75) Inventor: Revital Lifshitz-Liron, Hertzlia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/796,686

(22) Filed: Apr. 27, 2007

(65) Prior Publication Data

US 2007/0259964 A1 Nov. 8, 2007

Related U.S. Application Data

(60) Provisional application No. 60/796,318, filed on Apr. 27, 2006, provisional application No. 60/799,504, filed on May 10, 2006.

(51) Int. Cl.
*C07C 211/00* (2006.01)

(52) U.S. Cl. ............................ 564/337; 560/28; 560/41; 564/342; 564/343; 564/133; 564/134; 564/182

(58) Field of Classification Search ................ 564/337, 564/342, 343, 133, 134, 139, 142, 182; 560/41
See application file for complete search history.

(56) References Cited

U.S. PATENT DOCUMENTS

| | | | |
|---|---|---|---|
| 4,966,988 A | 10/1990 | Schinski et al. | |
| 5,648,541 A | 7/1997 | Van Wagenen et al. | |
| 6,011,068 A | 1/2000 | Nemeth et al. | |
| 6,031,003 A | 2/2000 | Nemeth et al. | |
| 6,211,244 B1 * | 4/2001 | Van Wagenen et al. | |
| 6,313,146 B1 | 11/2001 | Van Wagenen et al. | |
| 2005/0147669 A1 | 7/2005 | Lawrence et al. | |
| 2005/0234261 A1 | 10/2005 | Wilken et al. | |
| 2006/0276534 A1 | 12/2006 | Martin et al. | |

FOREIGN PATENT DOCUMENTS

WO   WO 2006/125026   11/2006

OTHER PUBLICATIONS

Devasher et al., "Aqueous-Phase, Palladium-catalyzed cross-coupling of aryl bromides under mild conditions, using water soluable, sterically demanding alkylphosphines", Journal of Organic Chemistry, American Chemical Society, vol. 69, 2004, pp. 7919-7927.
Anonymous, "N-[1-(R)-(-)-(1-naphthyl)]-3-[3-[3-(trifluoromethyl)phenyl]-1-aminopropane hydrochloride", IP.com Journal, May 23, 2005, XPO002424259.
"Sensipar (Cinacalcet HCl) Tablets" Summary Basis of Approval of New Drug Application #21-688 By FDA, (2004).
Iqbal et al., "Cinacalcet Hydrochloride" *IDrugs*, vol. 6, No. 6, p. 587-592, (2003).
Snyder et al., *Introduction To Modern Liquid Chromatography*, 2nd Ed., (1979), pp. 549-572, John Wiley & Sons, Inc.
Strobel et al., *Chemical Instrumentation: A Systematic Approach*, 3rd Ed., (1989), pp. 391-393, 879-894, 922-925, 953.
Database Belistein; Belistein Institute for Organic Chemistry, Frankfurt-Main, DE; XP002451055 (& Pharmazie, vol. 59, No. 10, 2004, pp. 744-752).
"Cinacalcet Hydrochloride: Treatment of Hyperparathyroidism", Drugs of the Future (2002) 27 (9):831-836.
Wang et al., "Synthesis of Cinacalcet congeners", Tetrahedron Letters (2004) 45:8355-8358.

\* cited by examiner

*Primary Examiner*—Yvonne Eyler
*Assistant Examiner*—Sudhakar Katakam
(74) *Attorney, Agent, or Firm*—Kenyon & Kenyon LLP

(57) ABSTRACT

Provided is a process for preparing Cinacalcet, (R)-α-methyl-N-[3-[3-(trifluoromethyl)phenyl]propyl]-1-naphthalenemethane amine and intermediates thereof.

42 Claims, No Drawings

PROCESS FOR THE PREPARATION OF CINACALCET BASE

CROSS-REFERENCE TO RELATED APPLICATIONS

This application claims the benefit of priority to U.S. provisional Application Ser. Nos. 60/796,318, filed Apr. 27, 2006, and 60/799,504, filed May 10, 2006, hereby incorporated by reference.

FIELD OF THE INVENTION

The invention encompasses a process for preparing Cinacalcet, (R)-α-methyl-N-[3-[3-(trifluoromethyl)phenyl]propyl]-1-naphthalenemethane amine and intermediates thereof.

BACKGROUND OF THE INVENTION (R)-α-methyl-N-[3-[3-(trifluoromethyl)phenyl]propyl]-1-naphthalenemethane amine, ("CNC-base," "cinacalcet base," or "cinacalcet") has the following formula:

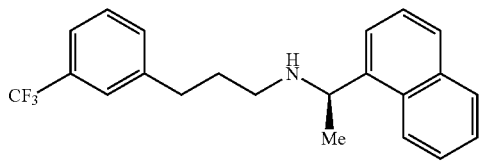

and a CAS number of 226256-56-0. This molecule is the free base form of Cinacalcet hydrochloride, $C_{22}H_{22}F_3N \cdot HCl$. Cinacalcet hydrochloride, herein CNC-HCl has a molecular weight of 393.9 and CAS number 364782-34-3. CNC-HCl is marketed as SENSIPAR™, and is the first drug in a class of compounds known as calcimimetics to be approved by the FDA.

Calcimimetics are a class of orally active, small molecules that decrease the secretion of parathyroid hormone ("PTH") by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of PTH, an indicator of secondary hyperparathyroidism, are associated with altered metabolism of calcium and phosphorus, bone pain, fractures, and an increased risk for cardiovascular death.

CNC-HCl is approved for treatment of secondary hyperparathyroidism in patients with chronic kidney disease on dialysis. Treatment with CNC-HCl lowers serum levels of PTH as well as the calcium/phosphorus ion product, a measure of the amount of calcium and phosphorus in the blood.

U.S. Pat. No. 6,011,068 discloses calcium receptor-active molecules, such as those having the general structure of cinacalcet. U.S. Pat. No. 6,211,244 ("'244 patent") discloses calcium receptor-active compounds related to cinacalcet and methods of preparing such compounds. Using the methods disclosed in the '244 patent, as well as DRUGS OF THE FUTURE (2002) 27(9):831, the desired cinacalcet enantiomer, may be produced by reacting 3-[3-(trifluoromethyl)phenyl]propylamine with 1-acetyl naphthalene in the presence of titanium (IV) isopropoxide, to produce an imine corresponding to cinacalcet, followed by treatment with ethanolic or methanolic sodium cyanoborohydride, and resolution of the racemic Cinacalcet base by chiral liquid chromatography, as depicted in the following scheme:

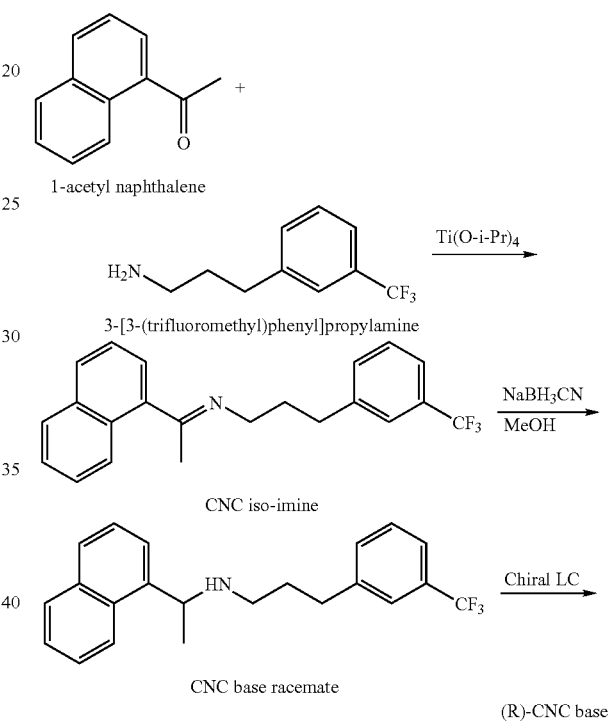

However, this process involved the use of flammable and highly toxic reagents, such as titanium (IV) isopropoxide and ethanolic or methanolic sodium cyanoborohydride.

In another process disclosed in the '244 patent, cinacalcet may be produced by treating 3-trifluoromethylcinnamonitrile with diisobutyl aluminum hydride, followed by treatment of the intermediate aluminum-imine complex with (R)-1-(1-naphthyl)ethylamine, and reduction of the intermediate imine with ethanolic sodium cyanoborohydride, according to the following scheme:

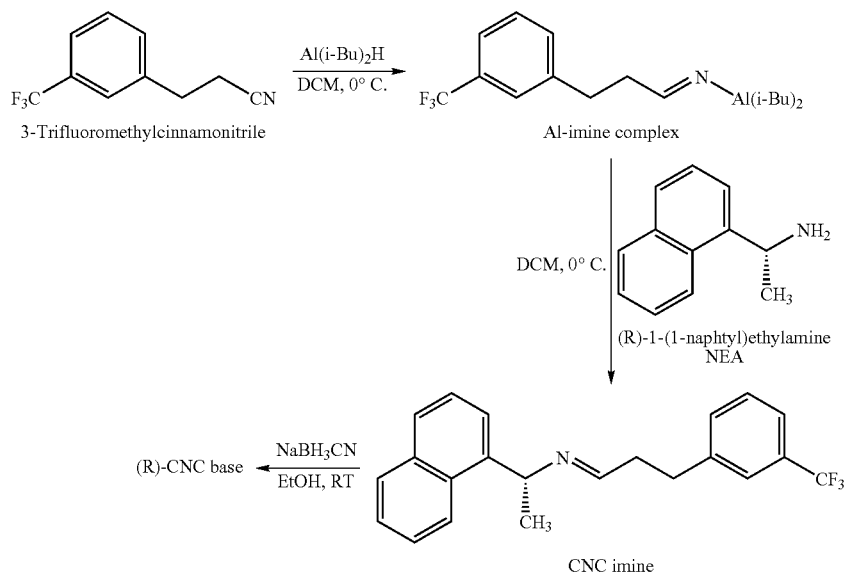

However, synthesis of the 3-trifluoromethylcinnamonitrile precursor in this process is disclosed only in Tetrahedron Letters (2004) 45:8355.

Similarly, using the process disclosed in the '244 patent, as well as DRUGS OF THE FUTURE (2002) 27 (9): 831 the desired Cinacalcet enantiomer may be produced by reacting (R)-1-(1-naphthyl)ethylamine with 3-[3-(trifluoromethyl)phenyl]propionaldehyde in the presence of titanium (IV) isopropoxide to produce the imine that corresponds to Cinacalcet, followed by treatment with ethanolic sodium cyanoborohydride, according to the following scheme:

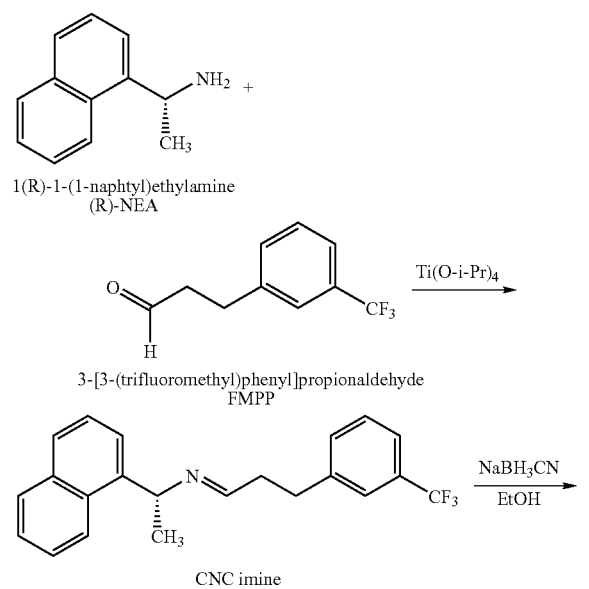

However, the processes mentioned require the use of reagents such as titanium (IV) isopropoxide and ethanolic sodium cyanoborohydride which are highly flammable, difficult to handle, toxic reagents.

Moreover, the only synthetic route known to the precursor of CNC-base, 3-[3-(trifluoromethyl)phenyl]propionaldehyde is disclosed in Tetrahedron Letters (2004) 45:8355 and is described in the following scheme:

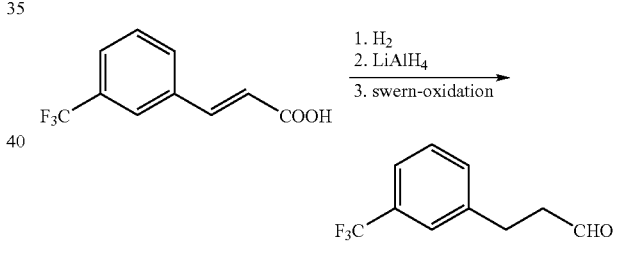

by reduction of the double bond of the corresponding Cinnamic acid derivative, followed by reduction of the carboxylic acid moiety to the corresponding alcohol, which is then oxidized to the aldehyde by Swern-oxidation, using non-environmental friendly reagents, such as oxalyl chloride and DMSO.

Thus, there is a need in the art for an improved process for the preparation of CNC-base and salts thereof, preferably, the hydrochloride salt. The present invention provides such an alternative.

SUMMARY OF THE INVENTION

In one embodiment, the invention encompasses a process for preparing cinacalcet comprising: (a) reducing 3-trifluoromethyl cinnamic acid to obtain 3-[3-(trifluoromethyl)phenyl]propanoic acid; (b) converting the 3-[3-(trifluoromethyl)phenyl]propanoic acid into a compound of the following formula III

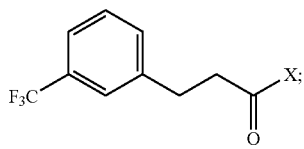

(c) combining the compound of formula III with (R)-1-naphthylethyl amine in the presence of a base to obtain N-[(1S)-1-(1-naphthyl)ethyl]-3-[3-trifluoromethyl)phenyl]propanamide; and (d) reducing the N-[(1S)-1-(1-naphthyl)ethyl]-3-[3-trifluoromethyl)phenyl propanamide to obtain cinacalcet, wherein X is carboxyl, alkoxy, halogen, or sulfonyl.

In another embodiment, the invention encompasses a process for preparing 3-[3-(trifluoromethyl)phenyl]propanoic acid, comprising reducing 3-trifluoromethyl cinnamic acid to obtain 3-[3-(trifluoromethyl)phenyl]propanoic acid.

In another embodiment, the invention encompasses a process for preparing a compound of the following formula III comprising: (a) dissolving 3-[3-(trifluoromethyl)phenyl]propanoic acid in a solvent selected from the group consisting of dichloromethane, toluene, acetonitrile and tetrahydrofuran to form a solution; and (b) combining the solution with a reagent selected from the group consisting of (i) a $C_1$ to $C_4$ carboxylic acid to obtain the compound of formula III wherein X is carboxyl; (ii) a $C_1$-$C_4$ alcohol in the presence of an acid, diazomethane, or dimethyl sulfate to obtain the compound of formula III wherein X is alkoxy; (iii) thionyl chloride, thionyl bromide, phosphorous pentachloride, phosphorous trichloride, oxalyl chloride, phosphorous pentabromide, phosphorous tribromide or oxalyl bromide to obtain the compound of formula III wherein X is halogen; and (iv) methanesulfonyl chloride, p-toluenesulfonyl chloride, 4-nitrobenzenesulfonyl chloride, or benzenesulfonyl chloride to obtain the compound of formula III wherein X is sulfonyl.

In another embodiment, the invention encompasses a process for preparing N-[(1S)-1-(1-naphthyl)ethyl]-3-[3-trifluoromethyl)phenyl]propanamide, comprising combining a compound of the following formula III with (R)-1-naphthylethyl amine in the presence of a base to obtain N-[(1S)-1-(1-naphthyl)ethyl]-3-[3-trifluoromethyl)phenyl]propanamide, wherein X is carboxyl, alkoxy, halogen, or sulfonyl.

In another embodiment, the invention encompasses N-[(1S)-1-(1-naphthyl)ethyl]-3-[3-trifluoromethyl)phenyl]propanamide.

In another embodiment, the invention encompasses a process for preparing cinacalcet, comprising reducing N-[(1S)-1-(1-naphthyl)ethyl]-3-[3-trifluoromethyl)phenyl propanamide to obtain cinacalcet.

In another embodiment, the invention encompasses a process for preparing a pharmaceutically acceptable acid addition salt of cinacalcet, comprising: (a) preparing cinacalcet by any of the above-described processes, and (b) converting the cinacalcet into a pharmaceutically acceptable acid addition salt of cinacalcet. Preferably, the pharmaceutically acceptable acid addition salt is a hydrochloride salt.

DETAILED DESCRIPTION OF THE INVENTION

The invention addresses the above-described shortcomings of the prior art by providing an improved process for preparing cinacalcet. The process can be illustrated by the following Scheme 1.

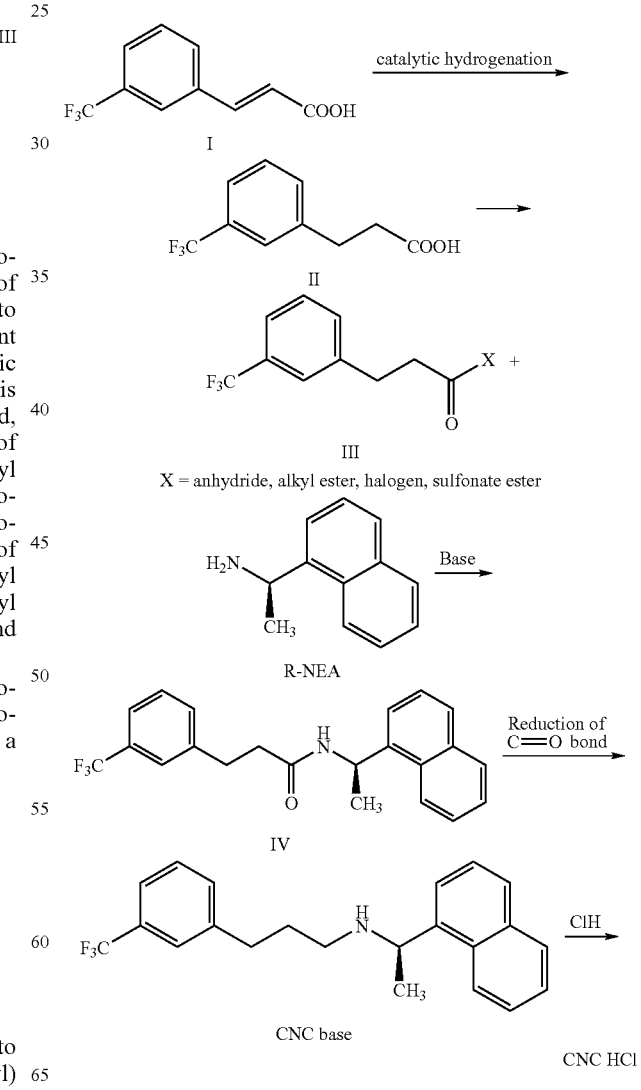

The process comprises: (a) reducing 3-trifluoromethyl cinnamic acid ("compound I") to obtain 3-[3-(trifluoromethyl)phenyl]propanoic acid ("compound II"); (b) converting the compound II into a compound of the following formula III

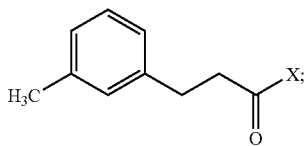

III (c) combining the compound of formula III with (R)-1-naphtylethyl amine ("R-NEA") in the presence of a base to obtain N-[(1S)-1-(1-naphthyl)ethyl]-3-[3-(trifluoromethyl)phenyl]propanamide ("compound IV"); and (d) reducing the compound IV to obtain cinacalcet, wherein X is carboxyl, alkoxy, halogen, or sulfonyl.

Preferably, compound I is reduced by hydrogenation to obtain compound II. More preferably, compound I is reduced by catalytic hydrogenation (i.e., with hydrogen in the presence of catalyst). The catalytic hydrogenation may be performed by any method known to one of ordinary skill in the art. For example, compound I may be dissolved in a lower alcohol, i.e., a $C_1$-$C_4$ aliphatic, straight chain or branched alcohol, and exposed to $H_2$ pressure in the presence of a catalyst that includes, but is not limited to, Pd/C or $PtO_2$ (Adam's catalysts) or Raney nickel. When Pd/C or $PtO_2$ is used, the $H_2$ pressure is preferably 1 atmosphere. When Raney nickel is used, the $H_2$ pressure is moderately high (~1000 psi). Preferably, the hydrogenation is carried out over a period of about 5 to about 24 hours, and more preferably about 5 to about 10 hours, to obtain compound II. Compound II may then be recovered by any method known to one of skill in the art.

The compound II thus prepared may be used to prepare any downstream intermediate (i.e., the compound of formula III or compound IV) or cinacalcet base. The cinacalcet base can then be converted into an acid addition salt, preferably cinacalcet hydrochloride, crystalline forms, and solvates thereof.

Preferably, compound II is converted into the compound of formula III by a process, comprising: (a) dissolving compound II in a solvent selected from the group consisting of dichloromethane ("DCM"), toluene, acetonitrile and tetrahydrofuran ("THF") to form a solution; and (b) combining the solution with a suitable reagent to form the compound of formula III.

When X is carboxyl (i.e., the compound of formula III is an acid anhydride), the reagent is preferably a $C_1$ to $C_4$ carboxylic acid.

When X is alkoxy (i.e., the compound of formula III is an alkyl ester), the reagent is preferably a $C_1$-$C_4$ alcohol in the presence of an acid (e.g., HCl, $H_2SO_4$), diazomethane, or dimethylsulfate. The alcohol is chosen based on the alkyl group desired. For example, for the methyl ether, one would dissolve the compound II in methanol, while, for ethyl ether, one would dissolve compound II in ethanol.

When X is halogen (i.e., the compound of formula III is an acid halide), the reagent is preferably selected from the group consisting of thionyl chloride ($SOCl_2$), thionyl bromide ($SOBr_2$), phosphorous pentachloride ($PCl_5$), phosphorous trichloride ($PCl_3$), phosphorous pentabromide ($PBr_5$), phosphorous tribromide ($PBr_3$), oxalyl chloride [$(COCl)_2$], and oxalyl bromide [$(COBr)_2$], in the presence of an acid (HCl, $H_2SO_4$). When thionyl chloride ($SOCl_2$) or thionyl bromide ($SOBr_2$) are used as reagents, a catalyst is present, such as DMF.

When X is sulfonyl (i.e., the compound of formula III is a sulfonate ester), the reagent is preferably selected from the group consisting of methanesulfonyl chloride ("MsCl"), p-toluenesulfonyl chloride ("TsCl"), 4-nitrobenzenesulfonyl chloride (nosyl chloride; "NsCl"), and benzenesulfonyl chloride.

Preferably, the conversion of compound II into the compound of formula III is carried out at a temperature of about 0° C. to about 50° C. Preferably, the conversion is accomplished over a time period of about 0.5 to about 24 hours, however the appropriate time and temperature will vary based on the other parameters, such as reagent choice. The compound III may be recovered by any method known to one of skill in the art.

The compound of formula III thus prepared may be used to prepare any downstream intermediate (i.e., compound IV) or cinacalcet base. The cinacalcet base can then be converted into an acid addition salt, preferably cinacalcet hydrochloride, crystalline forms, and solvates thereof.

Preferably, the compound of formula III is converted into compound IV by a process, comprising combining the compound of formula III with R-NEA in the presence of a base to obtain compound IV. Preferably, the compound of formula III is combined with R-NEA in the presence of a solvent. Preferably, the solvent is selected from the group consisting of acetonitrile, toluene, isopropyl alcohol ("IPA"), ethanol, ethyl acetate, methyl iso-butyl ketone ("MIBK"), and acetone, and more preferably acetonitrile or toluene.

The base can be any organic or inorganic base. Suitable bases include, but are not limited to, carbonates and tri-($C_2$ to $C_4$ alkyl)amines.

Preferably, the combination is heated to obtain compound IV. More preferably, the combination is heated at the reflux temperature of the solvent, for example from about 56° C. to about 130° C. Preferably, the combination is maintained for about 7 to about 90 hours to obtain compound IV, depending upon the solvent used. As a general rule, the higher the temperature, the shorter the reaction time. Compound IV is then extracted with a suitable organic solvent such as a $C_4$ to $C_8$ ether, DCM, EtOAc, toluene.

The compound IV thus prepared may be used to prepare cinacalcet base. The cinacalcet base can then be converted into an acid addition salt, preferably cinacalcet hydrochloride, crystalline forms, and solvates thereof.

Preferably, compound IV is reduced with $BH_3$. Preferably, the reduction is performed in the presence of a solvent. Suitable solvents include, but are not limited to $C_4$ to $C_8$ aliphatic, branched or cyclic ethers, such as methyl-tert-butyl ether ("MTBE") and tetrahydrofuran ("THF"). Preferably, the solvent is THF.

Preferably, the reduction of compound IV is performed at a temperature of about 0° to about 5° C. Preferably, the reduction is performed over a period of about 16 to about 24 hours to obtain cinacalcet base.

The cinacalcet base thus prepared may be converted into a pharmaceutically acceptable acid addition salt, preferably cinacalcet hydrochloride, or other polymorphic crystalline forms and solvates thereof The cinacalcet base may be converted into cinacalcet hydrochloride by any method known to one of ordinary skill in the art. Such methods include, but are not limited to, reacting the cinacalcet base with hydrogen chloride. Preferably, the cinacalcet base is dissolved in an organic solvent and combined with an aqueous solution or gaseous hydrogen chloride to obtain cinacalcet hydrochloride. Preferably, the organic solvent is selected from aliphatic or branched lower alcohols ($C_1$-$C_6$), ketones, esters, ethers $C_4$-$C_8$ cyclic or aliphatic (such as, diethyl ether, MTBE), aliphatic or branched $C_1$-$C_8$ alkanes.

Having thus described the invention with reference to particular preferred embodiments and illustrative examples, those in the art would appreciate modifications to the invention as describes and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinal skill in the art and are described in numerous publications. All references mentioned herein are incorporated in their entirety.

EXAMPLES

Example 1

An ethanolic solution of 3-Trifluoromethyl cinnamic acid (I) is dissolved in absolute Ethanol (5 volumes per gram of 3-Trifluoromethyl cinnamic acid) and hydrogenated (1 atm of $H_2$) in the presence of palladium on carbon (10% w/w of starting material) for 16 hours at room temperature. Then the catalyst is filtered out and the solvent is evaporated until dryness to obtain saturated carboxylic acid (II).

Example 2

A flask flushed with nitrogen is charged with saturated carboxylic acid (II), Thionyl chloride (1.1 eq), Toluene [6 volumes per gram of (II)] and a catalytic amount of DMF [0.5% w/w relative to (II)]. The reaction mixture is heated to 45° to 50° C. for 2 hours. The solvent and excess Thionyl chloride are removed under reduced pressure until dryness to obtain an acid chloride (III).

Example 3

The acid chloride (III) is dissolved in Acetonitrile [4 volumes per gram of (III)]. (R)-1-Naphtylethyl amine (1.0 eq) and anhydrous $K_2CO_3$ (1.0 eq) are added and the reaction mixture is heated to reflux temperature for about 22 hours. Then salts are filtered out and the solvent is removed under reduced pressure. The residue is dissolved in Toluene (7 volumes per gram of residue after evaporation) and 32% HCl (2 volumes per gram of residue after evaporation) to obtain pH=0-1. The organic phase is then washed with water (2-3× 1.5 volumes per gram of residue after evaporation). The solvent is evaporated under reduced pressure until dryness to give the amide (IV).

Example 4

The amide (IV) is dissolved in THF [30 volumes per gram of amide (IV)]. The solution is cooled to 0° C. and a 1M solution of $BH_3$ in THF (2.5 eq) is added drop-wise. The reaction mixture is allowed to warm to room temperature and stirred at this temperature for 16 hours. Then it is quenched carefully with 6.0M aqueous HCl and heated to reflux for 1 hour. After cooling to room temperature, the mixture is basified with 1.0N aqueous NaOH. The phases are separated and the aqueous layer is extracted with EtOAc. The combined organic phase is dried over $MgSO_4$, filtered and the solvent is removed under reduced pressure to obtain Cinacalcet base which can be used as it is for the next step or can be purified by column chromatography on silica gel using a gradient from Dichloromethane to a mixture of 2.5-5% Methanol/ 97.5-95% Dichloromethane as eluent.

Example 5

Cinacalcet base is dissolved in absolute Ethanol (4 volumes per gram of Cinacalcet base). Then 1N HCl (1.5 eq) is added drop-wise. The obtained mixture is stirred at room temperature for 20 hours to obtain a precipitate. The product is isolated by filtration, washed with water, and dried in a vacuum oven at 50° C. for 24 hours to obtain Cinacalcet hydrochloride.

Example 6

Cinacalcet base is dissolved in MTBE (20 volumes per gram of Cinacalcet base). Then HCl gas (2 eq) is bubbled into the solution at room temperature. The obtained slurry is stirred for 2 hours at room temperature. The product is isolated by filtration, washed with MTBE, and dried in a vacuum oven at 50° C. for 24 hours to obtain Cinacalcet hydrochloride.

What is claimed is:

1. A process for preparing cinacalcet, comprising:
    a) reducing 3-trifluoromethyl cinnamic acid to obtain 3-[3-(trifluoromethyl) phenyl]propanoic acid;
    b) optionally, converting the 3-[3-(trifluoromethyl)phenyl] propanoic acid into a compound of formula III

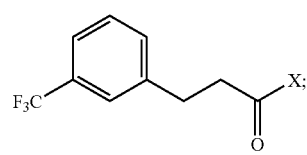

c) converting the 3-[3-(trifluoromethyl)phenyl]propanoic acid into N-[(1S)-1-(1-naphthyl)ethyl]-3-[3-trifluoromethyl)phenyl]propanamide, or combining the compound of formula III with (R)-1-naphthylethyl amine in the presence of a base to obtain N-[(1S)-1-(1-naphthyl) ethyl]-3-[3-trifluoromethyl)phenyl]propanamide; and
    d) reducing the N-[(1S)-1-(1-naphthyl)ethyl]-3-[3-trifluoromethyl)phenyl propanamide to obtain cinacalcet,
    wherein X is carboxyl, alkoxy, halogen, or sulfonyl.

2. A process for preparing a pharmaceutically acceptable acid addition salt of cinacalcet, comprising:
    a) preparing cinacalcet by the process of claim 1; and
    b) converting the cinacalcet into a pharmaceutically acceptable acid addition salt of cinacalcet.

3. The process of claim 2, wherein the a pharmaceutically acceptable acid addition salt is a hydrochloride salt.

4. The process of claim 1, wherein the 3-trifluoromethyl cinnamic acid is reduced with hydrogen in the presence of a catalyst.

5. The process of claim 4, wherein the catalyst is palladium on carbon, platinum dioxide, or Raney nickel.

6. The process of claim 4, wherein the reduction is performed over a period of about 5 to about 24 hours.

7. The process of claim 4, wherein the hydrogen is present at a pressure of about 1 atmosphere to about 1000 psi.

8. The process according to claim 1, further comprising converting the 3-[3-(trifluoromethyl)phenyl]propanoic acid into the compound of formula III.

9. The process according to claim 1, further comprising converting the 3-[3-(trifluoromethyl)phenyl]propanoic acid into N-[(1S)-1-(1-naphthyl)ethyl]-3-[3-trifluoromethyl)phenyl]propanamide.

10. A process for preparing cinacalcet, comprising:
   a) reducing 3-trifluoromethyl cinnamic acid to 3-[3-(trifluoromethyl)phenyl]propanoic acid;
   b) converting the 3-[3-(trifluoromethyl)phenyl]propanoic acid into cinacalcet.

11. A process for preparing a pharmaceutically acceptable acid addition salt of cinacalcet, comprising:
   a) preparing cinacalcet by the process of claim 10; and
   b) converting the cinacalcet into a pharmaceutically acceptable acid addition salt of cinacalcet.

12. The process of claim 11, wherein the pharmaceutically acceptable acid addition salt is a hydrochloride salt.

13. The process according to claim 1, further comprising preparing a compound of formula III

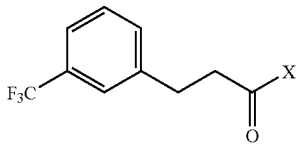

in a process, comprising:
   a) dissolving 3-[3-(trifluoromethyl)phenyl]propanoic acid in a solvent selected from the group consisting of dichloromethane, toluene, acetonitrile and tetrahydrofuran to form a solution; and
   b) combining the solution with a reagent selected from the group consisting of
      i) a $C_1$ to $C_4$ carboxylic acid to obtain the compound of formula III wherein X is carboxyl;
      ii) a $C_1$-$C_4$ alcohol in the presence of an acid, diazomethane, or dimethylsulfate to obtain the compound of formula III wherein X is alkoxy;
      iii) thionyl chloride, thionyl bromide, phosphorous pentachloride, phosphorous trichloride, oxalyl chloride, phosphorous pentabromide, phosphorous tribromide, or oxalyl bromide to obtain the compound of formula III wherein X is halogen; and
      iv) methanesulfonyl chloride, p-toluenesulfonyl chloride, 4-nitrobenzenesulfonyl chloride, or benzenesulfonyl chloride to obtain the compound of formula III wherein X is sulfonyl.

14. The process of claim 13, wherein the combination is performed at a temperature of about 0° C. to about 50° C.

15. The process of claim 13, wherein the combination is maintained for about 0.5 hours to about 24 hours to obtain the compound of formula III.

16. A process for preparing N-[(1S)-1-(1-naphthyl)ethyl]-3-[3-trifluoromethyl)phenyl]propanamide, comprising:
   a) preparing the compound of formula III by the process of claim 13; and
   b) converting the compound of formula III into N-[(1S)-1-(1-naphthyl)ethyl]-3-[3-trifluoromethyl)phenyl]propanamide.

17. A process for preparing cinacalcet, comprising:
   a) preparing the compound of formula III by the process of claim 13; and
   b) converting the compound of formula III into cinacalcet.

18. A process for preparing a pharmaceutically acceptable acid addition salt of cinacalcet, comprising:
   a) preparing cinacalcet by the process of claim 17; and
   b) converting the cinacalcet into a pharmaceutically acceptable acid addition salt of cinacalcet.

19. The process of claim 18, wherein the pharmaceutically acceptable acid addition salt is a hydrochloride salt.

20. The process according to claim 1, further comprising preparing N-[(1S)-1-(1-naphthyl)ethyl]-3-[3-trifluoromethyl)phenyl]propanamide in a process, comprising combining a compound of the following formula III

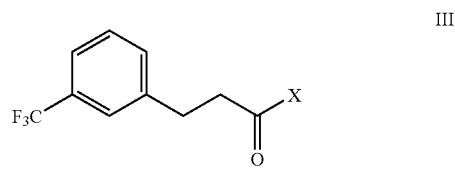

with (R)-1-naphthylethyl amine in the presence of a base to obtain N-[(1S)-1-(1-naphthyl)ethyl]-3-[3-trifluoromethyl)phenyl]propanamide, wherein X is carboxyl, alkoxy, halogen, or sulfonyl.

21. The process of claim 20, further comprising combining the compound of formula III, the (R)-1-naphthylethyl amine, and the base with a solvent.

22. The process of claim 21, wherein the solvent is selected from the group consisting of acetonitrile, toluene, isopropyl alcohol, ethanol, ethyl acetate, methyl iso-butyl ketone, and acetone.

23. The process of claim 20, wherein the base is an organic or inorganic base.

24. The process of claim 20, wherein the base is a carbonate or a tri-($C_2$ to $C_4$ alkyl)amine.

25. The process of claim 21, wherein the combination is heated to obtain the N-[(1S)-1-(1-naphthyl)ethyl]-3-[3-trifluoromethyl)phenyl]propanamide.

26. The process of claim 25, wherein the combination is heated at the reflux temperature of the solvent.

27. The process of claim 20, wherein the combination is maintained for about 7 to about 90 hours to obtain the N-[(1S)-1-(1-naphthyl)ethyl]-3-[3-trifluoromethyl)phenyl]propanamide.

28. N-[(1S)-1-(1-naphthyl)ethyl]-3-[3-trifluoromethyl)phenyl]propanamide, prepared by the process of claim 20.

29. A process for preparing cinacalcet, comprising:
   a) preparing N-[(1S)-1-(1-naphthyl)ethyl]-3-[3-trifluoromethyl)phenyl]propanamide by the process of claim 20; and
   b) converting the N-[(1S)-1-(1-naphthyl)ethyl]-3-[3-trifluoromethyl)phenyl]propanamide into cinacalcet.

30. A process for preparing a pharmaceutically acceptable acid addition salt of cinacalcet, comprising:
   a) preparing cinacalcet by the process of claim 29; and
   b) converting the cinacalcet into a pharmaceutically acceptable acid addition salt of cinacalcet.

31. The process of claim 30, wherein the pharmaceutically acceptable acid addition salt is a hydrochloride salt.

32. A process for preparing cinacalcet, comprising reducing N-[(1S)-1-(1-naphthyl)ethyl]-3-[3-trifluoromethyl)phenyl propanamide to obtain cinacalcet.

33. The process of claim 32, wherein the N-[(1S)-1-(1-naphthyl)ethyl]-3-[3-trifluoromethyl)phenyl propanamide is reduced with $BH_3$.

34. The process of claim 32, wherein the reduction is performed in the presence of a solvent.

35. The process of claim 34, wherein the solvent is selected from the group consisting of $C_4$ to $C_8$ aliphatic, branched or cyclic ethers.

36. The process of claim 35, wherein the solvent is methyl-tert butyl ether or tetrahydrofuran.

37. The process of claim 35, wherein the reduction is performed at a temperature of about 0° to about 5° C.

38. The process of claim 35, wherein the reduction is performed over a period of about 16 to about 24 hours.

39. A process for preparing a pharmaceutically acceptable acid addition salt of cinacalcet, comprising:
   a) preparing cinacalcet by the process of claim 32; and
   b) converting the cinacalcet into a pharmaceutically acceptable acid addition salt of cinacalcet.

40. The process of claim 39, wherein the pharmaceutically acceptable acid addition salt is a hydrochloride salt.

41. A process for preparing N-[(1S)-1-(1-naphthyl)ethyl]-3-3-trifluoromethyl)phenyl] propanamide, comprising:
   a) reducing 3-trifluoromethyl cinnamic acid to obtain 3-[3-(trifluoromethyl)phenyl]propanoic acid; and
   b) converting the 3-[3-(trifluoromethyl)phenyl]propanoic acid into N-[(1S)-1-(1-naphthyl)ethyl]-3-[3-trifluoromethyl)phenyl] propanamide.

42. A process for preparing N-[(1S)-1-(1-naphthyl)ethyl]-3-[3-trifluoromethyl)phenyl] propanamide, comprising:
   a) reducing 3-trifluoromethyl cinnamic acid to obtain 3-[3-(trifluoromethyl)phenyl]propanoic acid; and
   b) preparing N-[(1S)-1-(1-naphthyl)ethyl]-3-[3-trifluoromethyl)phenyl]propanamide from the 3-[3-(trifluoromethyl)phenyl]propanoic acid.

* * * * *

UNITED STATES PATENT AND TRADEMARK OFFICE
CERTIFICATE OF CORRECTION

PATENT NO.         : 7,449,603 B2
APPLICATION NO. : 11/796686
DATED                 : November 11, 2008
INVENTOR(S)       : Lifshitz-Liron It is certified that error appears in the above-identified patent and that said Letters Patent is hereby corrected as shown below:

Column 5, line 12, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 5, line 14, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 5, line 51, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 5, line 65, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 6, line 2, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 6, line 5, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 7, line 17, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 10, line 43, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

UNITED STATES PATENT AND TRADEMARK OFFICE
CERTIFICATE OF CORRECTION

PATENT NO. : 7,449,603 B2
APPLICATION NO. : 11/796686
DATED : November 11, 2008
INVENTOR(S) : Lifshitz-Liron It is certified that error appears in the above-identified patent and that said Letters Patent is hereby corrected as shown below:

Column 10, line 46, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 10, line 48, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 11, line 6, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 11, line 58, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 11, line 62, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 10, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 24, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 39, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

UNITED STATES PATENT AND TRADEMARK OFFICE
CERTIFICATE OF CORRECTION

PATENT NO. : 7,449,603 B2
APPLICATION NO. : 11/796686
DATED : November 11, 2008
INVENTOR(S) : Lifshitz-Liron It is certified that error appears in the above-identified patent and that said Letters Patent is hereby corrected as shown below:

Column 12, line 45, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 47, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 50, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 53, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 63, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 12, line 65, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 14, line 3, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 14, line 8, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

UNITED STATES PATENT AND TRADEMARK OFFICE
CERTIFICATE OF CORRECTION

PATENT NO. : 7,449,603 B2
APPLICATION NO. : 11/796686
DATED : November 11, 2008
INVENTOR(S) : Lifshitz-Liron It is certified that error appears in the above-identified patent and that said Letters Patent is hereby corrected as shown below:

Column 14, line 10, change
"N-[(1S)-1-(1-naphthyl)ethyl]-3-[3-trifluoromethyl)phenyl]propanamide" to
-- N-[(1R)-1-(1-naphthyl)ethyl]-3-[3-trifluoromethyl)phenyl]propanamide --

Column 14, line 14, change
"N-[(1S)-1-(1-naphthyl)ethyl]-3-[3-trifluoromethyl)phenyl]propanamide" to
-- N-[(1R)-1-naphthyl)ethyl]-3-[3-trifluoromethy)pheny]propanamide --

Signed and Sealed this

Thirty-first Day of March, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,449,603 B2                                             Page 1 of 1
APPLICATION NO. : 11/796686
DATED                 : November 11, 2008
INVENTOR(S)        : Lifshitz-Liron It is certified that error appears in the above-identified patent and that said Letters Patent is hereby corrected as shown below:

Column 5, line 56, change

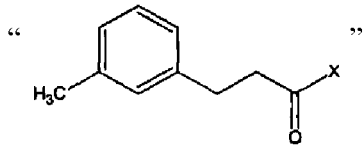

to

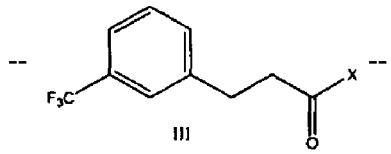

Column 7, line 7, change

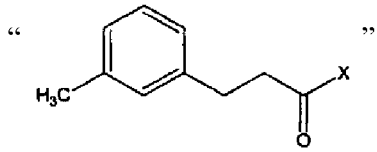

to

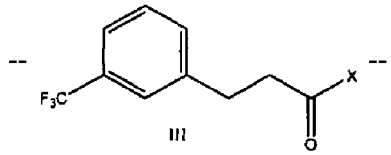

Signed and Sealed this

Twenty-fifth Day of August, 2009

David J. Kappos
*Director of the United States Patent and Trademark Office*